United States Patent [19]

Nakano et al.

[11] Patent Number: 5,956,657
[45] Date of Patent: Sep. 21, 1999

[54] METHOD FOR PRODUCING NITRO COMPOUNDS

[75] Inventors: Tatsuya Nakano, Himeji; Satoshi Sakaguchi, Suita; Yasutaka Ishii, 19-21, Besshohonmachi, Takatsuki-shi, Osaka 569, all of Japan

[73] Assignees: Daicel Chemical Industies, Ltd.; Yasutaka Ishii, both of Osaka, Japan

[21] Appl. No.: 08/997,585

[22] Filed: Dec. 23, 1997

[30] Foreign Application Priority Data

Dec. 27, 1996 [JP] Japan .................................. 8-349499

[51] Int. Cl.$^6$ .................................................. C07C 205/00
[52] U.S. Cl. ........................... 568/927; 568/941; 568/947
[58] Field of Search ..................... 568/947, 941, 568/927

[56] References Cited

U.S. PATENT DOCUMENTS 2,999,119   9/1961   McKinnis ................. 568/943
4,433,162   2/1984   Hamamoto et al. .

FOREIGN PATENT DOCUMENTS

0001922A1   6/1979   European Pat. Off. .
0497989A1   8/1992   European Pat. Off. .

OTHER PUBLICATIONS

Suzuki et al., J. Chem. Soc. Perkin Trans. 1, pp. 291–293 (1995).
N. Shuzo, Patent Abstracts of Japan, vol. 007, No. 227 (C–199)(JP 58 157748 A) abstract.
N. Shuzo, Patent Abstracts of Japan, vol. 007, No. 285 (C–201)(JP 58 162557 A) abstract.
Chemical Abstracts, vol. 109, No. 10, 81940a (Sep. 5, 1988).
Chemical Abstracts, vol. 81, No. 3, 13311z (Jul. 22, 1974).

*Primary Examiner*—Gary Geist
*Assistant Examiner*—J. Parsa
*Attorney, Agent, or Firm*—Birch, Stewart Kolasch & Birch, LLP

[57] ABSTRACT

The method provides nitro compounds at a high conversion and selectivity by nitrating substrates under comparatively mild conditions in the absence of catalysts. Organic substrates are nitrated using no catalysts or ozone, but using (1) at least one nitrogen compound selected from $N_2O$ or $NO$ and oxygen. It is advantageous for the nitration reaction to employ a nitrogen compound obtained by a reaction of the nitrogen compound with oxygen, particularly a nitrogen oxide comprising $N_2O_3$ as a main component. Additionally, organic substrates are nitrated using (2) $NO_2$. The substrates include a compound having a methine-carbon atom, and a compound having a methyl group or methylene group in an adjacent position to an aromatic ring.

5 Claims, No Drawings

METHOD FOR PRODUCING NITRO COMPOUNDS

FIELD OF THE INVENTION

The present invention relates to a method for producing nitro compounds, wherein use of nitrogen oxides ensures direct and efficient nitration of substrates.

BACKGROUND OF THE INVENTION

Nitro compounds are commonly utilised as a raw material for medicines, agricultural chemicals, dyes, solvents and explosives, a raw material for amino compounds, and the like. Nitration of hydrocarbons is generally conducted by a nitric acid process which employs a mixed acid (a mixture of nitric acid and sulfric acid). However, the nitric acid process requires a strong acid of high concentration in a large amount. Besides, since the nitration reaction is exothermic, it is difficult to improve its reaction operability. Furthermore, the nitric acid process by-produces large amounts of nitrogen oxides, which cause environmental pollutions and thus have to be treated in a proper manner.

As a nitration process, use of $N_2O_5$ and ozone in the presence of an iron catalyst has been suggested for nitration of aromatic compounds (e.g. toluene) and alicyclic compounds (e.g. adamantane). Due to the use of $NO_3$ as a reactant, this nitration process proceeds smoothly at a lower temperature. However, a catalyst should be incorporated in order to increase the reaction rate, and additional equipment such as an ozone generating apparatus should be installed for the generation of ozone.

SUMMARY OF THE INVENTION

It is, therefore, an object of the present invention to provide a method for producing nitro compounds, by which nitration can be conducted under comparatively mild conditions in the absence of catalysts and/or ozone.

Another object of the present invention is to provide a method for nitration, by which nitrogen oxides, which cause environmental pollutions, can be utilised effectively to provide nitro compounds at a high conversion and selectivity.

The inventors of the present invention have conducted intensive research to achieve the above objects, and found that substrates can be nitrated with the use of $N_2O_3$ obtained by a reaction of $N_2O$ and/or NO with oxygen, or the use of $N_2O$, without any catalysts or ozone.

The method of the present invention provides nitro compounds by nitrating organic substrates using at least one nitrogen compound selected from dinitrogen oxide and nitrogen monoxide as well as oxygen. This reaction can be conducted in the absence of catalysts. In this method, substrates are nitrated using a nitrogen oxide comprising, as a main component, $N_2O_3$ which is obtainable by a reaction of a nitrogen compound with oxygen. The substrate can be selected from a variety of saturated or unsaturated compounds, and may be any of aliphatic compounds, alicyclic compounds, aromatic compounds, and heterocyclic compounds. The substrate includes a compound having a methine-carbon atom, a compound having a methyl group or methylene group in an adjacent position to an aromatic ring.

The method of the present invention further includes a method for nitration which comprises reacting, with an organic substrate, a nitrogen oxide produced by a reaction of at least one nitrogen compound selected from dinitrogen oxide or nitrogen monoxide with oxygen.

The present invention also provides a method for producing nitro compounds, which method comprises contacting nitrogen dioxide with an organic substrate to give a corresponding nitro compound.

DETAILED DESCRIPTION OF THE INVENTION

In the method of the present invention, nitro compounds are produced by reacting nitrogen oxides with organic substrates.

The nitrogen oxides include (1) nitrogen oxides provided by a reaction of at least one nitrogen compound selected from dinitrogen oxide ($N_2O$) and nitrogen monoxide (NO) with oxygen, particularly $N_2O_3$ or a nitrogen oxide comprising $N_2O_3$ as a main component.

The nitrogen oxide $N_2O_3$ can be easily obtained by reacting $N_2O$ and/or NO with oxygen. To be more specific, $N_2O_3$ can be prepared by charging a reactor with nitrogen monoxide and oxygen to produce blue liquid $N_2O_3$.

The oxygen may be either pure oxygen or oxygen diluted with an inert gas (e.g. carbon dioxide, nitrogen, helium, argon). In addition, the oxygen source may be air.

In another embodiment of the present invention, the nitrogen oxides include (2) nitrogen dioxide ($NO_2$). With the use of $NO_2$, the nitration reaction proceeds smoothly even in the absence of oxygen, as a result of the contact with an organic substrate. Thus, oxygen is not essential in the reaction system using $NO_2$, but $NO_2$ can be used in the coexistence of oxygen.

The species of the substrate to be nitrated is not particularly limited. A broad range of saturated or unsaturated compounds are available, such as hydrocarbons (aliphatic hydrocarbons, alicyclic hydrocarbons, aromatic hydrocarbons), heterocyclic compounds, alcohols, ethers, esters, ketones, aldehydes, and so on. Preferred substrates include a compound having a methine-carbon atom, a compound having a methylene group at an adjacent position to an aromatic ring, and the like. In these substrates, a nitro group can be smoothly introduced into a methine-carbon atom or a carbon atom in a position adjacent to an aromatic ring (particularly in a benzyl position).

The compounds having a methine-carbon atom (methylidyne group) include, for example, chained hydrocarbons and bridged cyclic hydrocarbons having a tertiary carbon atom. As the chained hydrocarbons having a tertiary carbon atom, there may be mentioned aliphatic hydrocarbons having about 4 to 10 carbon atoms such as isobutane, isopentane, isohexane, 3-methylpentane, 2,3-dimethylbutane, 2-methylhexane, 3-methylhexane, 2,3-dimethylpentane, 2,4-dimethylpentane, 2,3,4-trimethylpentane, 3-ethylpentane, 2,3-dimethylhexane, 2,4-dimethylhexane, 3,4-dimethylhexane, 2,5-dimethylhexane, 2-propylhexane, 2-methylheptane, 4-methylheptane, 2-ethylheptane, 3-ethylheptane, 2,6-dimethylheptane, 2-methyloctane, 3-methyloctane, 2,7-dimethyloctane, 2-methylnonane, etc.

As the bridged cyclic hydrocarbons, there may be exemplified crosslinked cyclic hydrocarbons (e.g. bicyclic hydrocarbons such as decalin, hexahydroindane, carane, bornane, norbornene, vinyl norbornene, norbonadiene, norbornane, and formyl norbornene; tricyclic hydrocarbons such as homobredane, adamantane, methyladamantane, 1,3-dimethyladamantane, ethyladamantane, chloroadamantane, adamantanol, adamantanone, methyladamantanone, dimethyladamantanone, formyladamantane, and tricyclo $[4.3.1.1^{2,5}]$undecane; tetracyclic hydrocarbons such as tetracyclo$[4.4.0.1^{2,5}.1^{7,10}]$dodecane), dimers of dienes or their hydrogenated products (e.g. dicyclopentane, dicyclohexane, dicyclopentene, dicyclohexadiene, dicyclopentadiene), terpenes (e.g. limonene, menthene, pinane, pinene, menthol, camphor, bornene, caryophyllene, menthone), etc.

Desirable compounds having a methine-carbon atom (methylidyne group) include bridged cyclic hydrocarbons (or crosslinked cyclic hydrocarbons) having about 6 to 16 (particularly about 7 to 14) carbon atoms.

Examples of the compounds having a methyl group or methylene group at an adjacent position to an aromatic ring are aromatic hydrocarbons having an alkyl group (e.g. toluene, xylene, mesitylene, durene, ethylbenzene, propylbenzene, cumene, methylethylbenzene, methylnaphthalene, dimethylnaphthalene, methylanthracene, dimethylanthracene, trimethylanthracene, dibenzyl, diphenylmethane, triphenylmethane), heterocyclic compounds having an alkyl group (e.g. methylfuran, methylpyran, methylchroman, methylpyridine (picoline), dimethylpyridine (lutidine), trimethylpyridine (collidine), ethylpyridine, methylquinoline, methylindole, indane, indene, tetralin, fluorene), etc. Preferable compounds include compounds having a methyl group or having a methylene group in a benzyl position.

These substrates may be substituted with an appropriate substituent such as a hydroxyl group, an alkoxy group, a mercapto group, a carboxyl group, an alkoxycarbonyl group, a cycloalkyl group, an aryl group, a halogen atom, an amino group, an alkylamino group, an amide group, a nitro group, a nitrile group, an acyl group, an acylamino group, a sulfonyl group, a sulfinyl group, a sulfide group, a phosphino group, and the like.

The first feature of the present invention is to directly nitrate an organic substrate using no catalysts or ozone, but using (1) the nitrogen compounds (NO, $N_2O$) and oxygen. In particular, it is desirable to conduct direct nitration of a substrate using a nitrogen oxide ($N_2O_3$ or a nitrogen oxide comprising $N_2O_3$ as a main component) obtained by a reaction of a nitrogen compound with oxygen.

The amount of the nitrogen oxide (NO, $N_2O$, $N_2O_3$ or a nitrogen oxide comprising $N_2O_3$ as a main component) is selected in accordance with the amount of the introduced nitro group. For example, the amount of the nitrogen oxide is selected from a range of about 1 to 50 moles, preferably about 1.5 to 30 moles, and practically about 2 to 25 moles, in terms of $N_2O_3$, relative to 1 mole of the substrate.

The second feature of the present invention is to directly nitrate an organic substrate using (2) $NO_2$ (or a nitrogen oxide comprising $NO_2$ as a main component). No catalysts or ozone are required in this reaction, either.

The amount of the nitrogen dioxide $NO_2$ is selected likewise in accordance with the amount of the introduced nitro group. For example, the amount of the nitrogen dioxide $NO_2$ is selected from a range of about 1 to 50 moles, preferably about 1.5 to 30 moles, and practically about 2 to 25 moles relative to 1 mole of the substrate.

Additionally, the substrates may be nitrated by a method combining the methods (1) and (2). To be specific, nitration of organic substrates may be conducted in a reaction system in which (1) the nitrogen oxide (NO, $N_2O$) and oxygen (or, $N_2O_3$ or a nitrogen oxide comprising $N_2O_3$ as a main component) and (2) the nitrogen oxide comprising $NO_2$ as a main component are both present.

The nitration reaction can be conducted in the presence or absence of a solvent. As the solvent, use can be made of an inert solvent, examples of which are organic acids (e.g. carboxylic acids such as acetic acid and propionic acid), nitriles (e.g. acetonitrile, propionitrile, benzonitrile), amides (e.g. formamide, dimethylformamide), alcohols (e.g. ethanol, propanol, butanol, t-butanol, t-amylalcohol), aliphatic hydrocarbons (e.g. hexane, octane), aromatic hydrocarbons (e.g. benzene), organic halogen compounds (e.g. halogenated hydrocarbons such as dichloromethane, chloroform, dichloroethane, dichlorobenzene, and trifluoromethylbenzene; halogen-substituted carboxylic acids such as chloroacetic acid and trifluoroacetic acid; halogen-substituted acid anhydrides such as chloroacetic anhydride; halogen-substituted esters such as methyl chloroacetate and ethyl chloroacetate), nitro compounds (e.g. nitromethane, nitrobenzene), esters (e.g. ethyl acetate), ethers (e.g. dimethyl ether), and mixed solvents of these. Among them, carboxylic acids (e.g. acetic acid, propionic acid), organic halogen compounds and nitrites are preferred as the solvent. A mixture of two or more solvents serves to enhance the yield and selectivity. As the solvent mixtures, there may be mentioned a mixed solvent comprising at least one solvent selected from nitrites and organic halogen compounds (e.g. a mixed solvent of a nitrile and an organic halogen compound, a mixed solvent of a nitrile and an organic acid), and the like. When the solvents are used in combination, the ratio for blending these solvents can be selected from a wide range. For instance, the ratio of a dominant primary solvent relative to the other solvent(s) ranges from about 1/99 to 99/1 (former/the latter, by weight), preferably from about 5/95 to 95/5 (by weight), and more preferably about 10/90 to 90/10 (by weight) (e.g. 15/85 to 85/15 (by weight)).

The reaction temperature can be selected from a range of about 0° C. to 150° C., preferably about 30 to 125° C., and more preferably about 40 to 100° C. (particularly 50 to 100° C.), depending on the species of the substrate. The reaction according to the method of the present invention proceeds smoothly even under a comparatively low temperature, e.g. 40 to 75° C. The reaction pressure may be generally selected in the range of about 1 to 5 atm.

The reaction is conducted in a suitable atmosphere, for example, in the atmosphere of an inert gas (e.g. nitrogen, helium, argon), a nitrogen oxide, (e.g. NO, $N_2O$, $NO_2$), oxygen, air or the like.

The reaction may be conducted in any of a batch, semi-batch, or continuous system. After the completion of the reaction, the reaction product can be easily separated and purified by a conventional separation/purification method including such separation methods as filtration, concentration, distillation, extraction, crystallisation, recrystallisation, adsorption, column chromatography, and a combination of these separation methods.

Due to the use of nitrogen oxides instead of catalysts or ozone, substrates can be nitrated directly and efficiently even under comparatively mild conditions. Besides, the nitrogen oxides, which lead to environmental problems, are effectively utilised to give nitro compounds at a high conversion and selectivity.

EXAMPLES

The following examples are intended to describe the present invention in further detail and should by no means be interpreted as defining the scope of the invention.

Example 1

An eggplant-type side-arm flask (50 ml) was immersed in iced water to reduce the pressure therein, and nitrogen monoxide and oxygen were introduced into the flask from separate gas bags (3 L each). The flask was filled with reddish brown gas, and then blue liquid comprising $N_2O_3$ as a main component was produced while the reddish brown gas descended. The introduction of nitrogen monoxide and oxygen was repeated to give about 1.5 ml of the blue liquid, which was frozen with the use of liquid nitrogen.

The frozen blue liquid (1.8 g, 0.024 mole in terms of $N_2O_3$), adamantane (1 mmole), dichloroethane (6 ml) and acetonitrile (1.2 ml) were mixed and stirred in a nitrogen monoxide atmosphere at 60° C. for 14 hours. The reaction product was analysed by high-performance liquid chromatography to give nitroadamantane at a conversion of 90% and a yield of 78%.

Example 2

The frozen blue liquid (1.8 g, 0.024 mole in terms of $N_2O_3$), adamantane (1 mmole), dichloroethane (6 ml) and acetonitrile (1.2 ml) were mixed and stirred in an oxygen atmosphere at 60° C. for 14 hours. The reaction provided nitroadamantane at a conversion of 94% and a yield of 81%.

Example 3

Charged in a flask were adamantane (1 mmole), dichloroethane (6 ml), and acetonitrile (1.2 ml). With stirring, nitrogen monoxide and oxygen were charged into the flask from separate gas bags (1 L each), and the stirring was continued at 60° C. for 14 hours. The reaction product was analysed by high-performance liquid chromatography to give nitroadamantane at a conversion of 87% and a yield of 78%.

Example 4

The frozen blue liquid (1.8 g, 0.024 mole in terms of $N_2O_3$), toluene (2.6 g, 28 mmoles), dichloroethane (6 ml) and acetonitrile (1.2 ml) were mixed and stirred in a nitrogen monoxide atmosphere at 60° C. for 14 hours. The reaction provided nitromethylbenzene at a yield of 71% and nitrotoluene (a mixture of o- and p-nitrotoluene) at a yield of 2%, the conversion being 82%.

Example 5

Charged in a flask were toluene (2.6 g, 28 mmoles), dichloroethane (6 ml), and acetonitrile (1.2 ml). With stirring, nitrogen monoxide and oxygen were charged into the flask from separate gas bags (1 L each), and the stirring was continued at 60° C. for 14 hours. The reaction product was analysed by high-performance liquid chromatography to give nitromethylbenzene at a yield of 69% and nitrotoluene (a mixture of o- and p-nitrotoluene) at a yield of 1%, the conversion being 78%.

Example 6

The process of Example 1 was repeated except for using 1 mmole of ethylbenzene instead of 1 mmole of adamantane. With a conversion of 72%, the reaction provided (1-nitroethyl)benzene at a yield of 59%, and ethylnitrobenzene at a yield of 1%.

Example 7

Charged into a flask were adamantane (1 mmole), nitrogen dioxide $NO_2$ (2 ml), benzonitrile (6 ml), and acetic acid (1.2 ml), and the mixture was stirred in a nitrogen monoxide (NO) atmosphere at 60° C. for 12 hours. The reaction product was subjected to high-performance liquid chromatography to give nitroadamantane at a conversion of 97% and a yield of 66%.

Example 8

The process of Example 7 was repeated except for stirring in an oxygen atmosphere instead of a nitrogen monoxide (NO) atmosphere. The reaction provided nitroadamantane at a conversion of 99% and yield of 73%.

Example 9

The process of Example 7 was repeated except for stirring in an inert gas (argon) atmosphere instead of a nitrogen monoxide (NO) atmosphere. The reaction provided nitroadamantane at a conversion of 98% and a yield of 77%.

Example 10

Charged in a flask were adamantane (1 mmole), nitrogen dioxide $NO_2$ (1.2 ml), dichloroethane (6 ml), and acetonitrile (1.2 ml). With stirring, nitrogen monoxide and oxygen were charged into the flask from separate gas bags (1 L each), and the stirring was continued at 60° C. for 12 hours. The reaction product was analysed by high-performance liquid chromatography to give nitroadamantane at a conversion of 94% and a yield of 88%.

Example 11

Charged into a flask were adamantane (1 mmole), nitrogen dioxide $NO_2$ (15 mmoles), and trifluoromethylbenzene (3 ml). Then, the mixture was stirred in an oxygen atmosphere at 60° C. for 5 hours. The reaction product was subjected to high-performance liquid chromatography to give nitroadamantane at a conversion of 65% and a yield of 45%.

Example 12

Charged into a flask were adamantane (1 mmole), nitrogen dioxide $NO_2$ (15 mmoles), acetonitrile (1 ml) and trifluoromethylbenzene (2 ml). Then, the mixture was stirred in an oxygen atmosphere at 60° C. for 5 hours. The reaction product was subjected to high-performance liquid chromatography to give nitroadamantane at a conversion of 70% and a yield of 57%.

What is claimed is:

1. A method for producing nitro compounds comprising nitrating organic substrates, with (a) at least one nitrogen compound selected from the group consisting of dinitrogen oxide and nitrogen monoxide, and (b) oxygen;

wherein said organic substrates have (1) a methine-carbon atom, or said organic substrates have (2) a methyl group or methylene group in an adjacent position to an aromatic ring; at a reaction temperature of the nitration is 40 to 100° C.

2. A method for producing nitro compounds as claimed in claim 1, wherein said nitration is conducted with a nitrogen oxide which comprises $N_2O_3$ obtained by a reaction of the nitrogen compound with oxygen as a main component.

3. A method for producing nitro compounds which comprises reacting organic substrates having (1) a methine-carbon atom, or organic substrates having (2) a methyl group or methylene group in an adjacent position to an aromatic ring with a nitrogen oxide comprising $N_2O_3$ as a main component; wherein a nitro group is primarily introduced into a methine-carbon atom or a carbon atom in a benzyl position of the organic substrates;

at a reaction temperature of 40 to 100° C.

4. A method for nitration which comprises reacting (1) a nitrogen oxide produced by a reaction of (a) at least one nitrogen compound selected from the group consisting of dinitrogen oxide and nitrogen monoxide with (b) oxygen and (2) an organic substrate having (i) a methine-carbon atom, or an organic substrate having (ii) a methyl group or methylene group in an adjacent position to an aromatic ring; at a reaction temperature of 40 to 100° C.

5. A method for producing nitro compounds which comprises contacting nitrogen dioxide with an organic substrate having (1) a methine-carbon atom, or an organic substrates having (2) a methyl group or methylene group in an adjacent position to an aromatic ring at a temperature of 40 to 100° C.

* * * * *